United States Patent [19]

Yoshida

[11] Patent Number: 5,112,401
[45] Date of Patent: May 12, 1992

[54] CORRECTION FLUID FOR ELECTROPHOTO PLATES FOR OFFSET PRINTING

[75] Inventor: Hajime Yoshida, Aichi, Japan

[73] Assignee: Nikken Chemical Laboratory Co., Ltd., Nagoya, Japan

[21] Appl. No.: 493,418

[22] Filed: Mar. 14, 1990

[30] Foreign Application Priority Data

Mar. 23, 1989 [JP] Japan .................................. 1-71192

[51] Int. Cl.$^5$ ................................................ C07F 7/22
[52] U.S. Cl. .................................. 106/287.19; 252/527
[58] Field of Search ....................... 252/527, DIG. 11; 106/287.19

[56] References Cited

U.S. PATENT DOCUMENTS

| | | | |
|---|---|---|---|
| 3,234,124 | 2/1966 | Irani | 210/38 |
| 3,655,573 | 4/1972 | Carlson | 252/180 |
| 4,028,281 | 6/1977 | Millard et al. | 252/527 |
| 4,071,464 | 1/1978 | Quinlan | 252/180 |
| 4,579,720 | 4/1986 | Budnick | 423/10 |

FOREIGN PATENT DOCUMENTS 3235871 7/1983 Fed. Rep. of Germany .
55-103382 8/1980 Japan .
1-254962 10/1989 Japan .

*Primary Examiner*—Mark L. Bell
*Assistant Examiner*—Alan Wright
*Attorney, Agent, or Firm*—Spencer & Frank

[57] ABSTRACT

Disclosed is a correction fluid prepared by adding a stannous chelate compound having an acid phosphate ester of an aliphatic alcohol as a ligand to an aqueous acidic solution. The correction liquid forms a hydrophilic stannous chelate compound precipitate, when the pH value of the liquid is elevated. Accordingly, where the correction liquid is coated on the unnecessary line image part of an electrostatic master paper plate and the pH value of the thus coated liquid is elevated, the unnecessary line image part of the plate is to be coated with the hydrophilic and water-insoluble stannous chelate compound so that it becomes insensitive to ink. The operation for such correction may be effected at any stage before or after the lipophobication treatment of the electrostatic master paper plate to be corrected with the correction fluid.

21 Claims, No Drawings

CORRECTION FLUID FOR ELECTROPHOTO PLATES FOR OFFSET PRINTING

FIELD OF THE INVENTION

The present invention relates to a correction fluid which may partly erase the line image part on an electrophoto plate for offset printing. Erasure of line image part, as referred to herein means that the line image part is lipophobicated to eliminate the ink-sensitivity therefrom.

TECHNOLOGY REVIEW

A correction fluid which has a function of lipophobicating the unnecessary line image part on an electrophoto plate for offset printing thereby to eliminate the ink-affinity from the part has been developed along with the development of electrophoto plates. The procedure of the progress of such correction fluid will be explained in order hereunder.

(a) In the initial stage, a lipophilic powdery toner which is electrically charged by itself is sprayed over the charged part (line image part) of a master paper plate as coated with a photoelectroconductive zinc oxide (hereinafter referred to as "electrostatic master paper plate"), the toner is then fused onto the electrostatic master paper plate under heat, and thereafter the resulting electrostatic master paper plate is lipophobicated to finally prepare an electrophoto plate for offset printing.

In the initial stage, correction of the unnecessary line image part is effected by rubbing and removing the toner on the unnecessary line image part with cotton fibers or the like before the toner is hot-fused onto the electrostatic master paper plate.

(b) In the next stage, almost the same process as that of the above-mentioned initial stage is conducted for preparing the electrophotoplate for offset printing. However, because of progress of the platemaking devices to be used for the process, the step of spraying the toner over the line image part of the electrostatic master paper plate and the step of hot-fusing the toner onto the electrostatic master paper plate have come to be effected continuously. Accordingly, removal of the unnecessary toner prior to thermal fusion of the toner onto the electrostatic master paper plate could not be effected in the stage.

Under the situation, therefore, various correction fluids have been developed in the stage.

(1) The correction fluid as first developed is an organic solvent which may dissolve the toner and which has a property of not dissolving the binder in the zinc oxide layer of the electrostatic master paper plate. In other words, the toner as hot-fused onto the electrostatic master paper plate is dissolved by the correction fluid and the correction fluid is wiped off whereby the toner is removed from the line image part. However, the correction fluid of the kind has a drawback that it requires much time and troublesome labor for correction.

(2) The correction fluid as next developed is one consisting of ammonium phosphate as a hydrophilicating liquid and a heavy metal ion such as stannous ion as added to the liquid (refer to Japanese Patent Publication No. 48-5681). The correction fluid forms a hydrophilic and water-insoluble precipitate. Where the unnecessary line image part is coated with the precipitate, the coated part becomes hydrophilic and is therefore no more sensitive to ink.

Both the above-mentioned correction fluids (1) and (2) are used after the toner has been fixed onto the electrostatic master paper plate but before the electrostatic master paper plate is not lipophobicated.

However, a large-sized electrostatic master paper plate is often used in these days. Such large-sized electrostatic master paper is inconveniently handled with difficulty and "oil stains" as well as "fingerprints marks" would often adhere to the paper plate during handling thereof. If such "oil stains" and the like adhere to the hydrophilic non-line image part, the part would be sensitive to ink to thereby cause formation of some undesirable stains in the prints.

In order to prevent this as much as possible, a platemaker which has a lipophobicating device as combined therewith and which may therefore automatically lipophobicate the master plate has been developed. The electrostatic master paper plate as processed by the platemaker of the type is always already lipophobicated.

Where the above-mentioned correction fluids (1) and (2) are applied to such electrostatic master paper plate, the correction fluid must be coated on the unnecessary line image part and the electrostatic master paper plate is to be again lipophobicated. However, such would lose the meaning of the automatic lipophobication of the electrostatic master paper plate with the newly developed platemaker.

SUMMARY OF THE INVENTION

Under the situation, it is desired to provide a correction fluid which may eliminate the ink-sensitivity from the unnecessary line image part at any stage before or after the lipophobication treatment of the electrostatic master paper plate.

The present inventor tried to use various substances which are extremely highly hydrophilic and which are insoluble in water, such as acrylic acid polymers, metal oxides, silicate oxides and various proteins, as a correction fluid.

However, it has been found that these could not have a sufficient adhesion power to the line image part and therefore have some drawbacks that the layer of the substance to coat the line image part peels off or the layer breaks down after the plate has been used for printing for a long period of time. Therefore, the correction liquid comprising such substances is not practical.

Accordingly, the first object of the present invention is to provide a practically usable correction fluid at any stage before or after lipophobication of the electrostatic master paper plate.

In order to attain the object, a stannous chelate compound having an acidic phosphate ester of an aliphatic alcohol as a ligand is utilized in accordance with the present invention. Specifically, the said stannous chelate compound is previously dissolved in an aqueous acidic solution, and the aqueous solution (which is "correction liquid") is coated on the part to be corrected of the electrostatic master paper plate. After the pH value of the aqueous solution is elevated, the said stannous chelate compound precipitates out to form a hydrophilic and water-insoluble layer on the part to be corrected of the electrostatic master paper plate. Afterwards, the moisture content in the wetting water applied to the plate is adsorbed to the layer of the said chelate compound to form an aqueous film thereon, so that the part is no more sensitive to ink.

The second object of the present invention is to provide a correction fluid which may easily elevate the pH value thereof and which comprises a stannous chelate compound as dissolved in an aqueous acidic solution.

In order to attain the object, the acidic group of the aqueous acidic solution of the invention is volatile.

The third object of the present invention is to provide a correction fluid which is hardly hydrolyzed and which is adheres well to an electrostatic master paper plate.

In order to attain the object, a polar solvent is incorporated into the correction fluid which contains a stannous chelate compound as dissolved in an aqueous acidic solution, in accordance with the present invention.

The fourth object of the present invention is to provide a correction fluid which can smoothly be complexed or chelated with a lipophobicating solution, when it is used prior to lipophobication of an electrostatic master paper plate.

In order to attain the object, a dicarboxylic acid is incorporated into the correction fluid which contains a stannous chelate compound as dissolved in an aqueous acidic solution, in accordance with the present invention.

DETAILED DESCRIPTION OF THE INVENTION

The following are detailed descriptions of the constituents of the correction liquid of this invention.

Acidic phosphate esters of aliphatic alcohols for use in the present invention include, for example, acidic phosphate esters of aliphatic lower alcohols such as acidic methyl phosphate ($H_2PO_4CH_3$), acidic ethyl phosphate ($H_2PO_4CH_2CH_3$), acidic n-propyl phosphate ($H_2PO_4(CH_2)_2CH_3$) or acidic isopropyl phosphate ($H_2PO_4CH(CH_3)_2$), as well as acidic phosphate esters of alicyclic alcohols such as acidic inositol phosphate or phytic acid ($H_2PO_4)_6$), etc. One or more of such esters can be used as the chelating agent for forming the stannous chelate compound of the invention. In forming the chelate compound, the proportion of the both components (ester/stannous ion) is preferably (ester/stannous ion) of being from 0.5/1.0 to 1.0/1.0, from the viewpoint of the chelating equivalency therebetween. Most preferably, the chelating equivalency between them is 1/1. If the chelating equivalency of the ester is more than 1.0 or less than 0.5, the corrected part would unfavorably be stained.

The phosphate esters of aliphatic alcohols are to be a ligand for the stannous ion. The stannous ion having the acidic ester of aliphatic alcohol as a ligand is to be a water-insoluble white chelate precipitate having an extremely high hydrophilicity in an aqueous solution. However, where the hydrogen ion concentration in the aqueous solution increases (or that is, the pH value of the solution decreases), the precipitate would be converted into a water-soluble chelate so that the precipitate disappears. Where the hydrogen ion concentration of the solution is lowered (or the pH value thereof is elevated), the chelate is to be water-insolbule to again form a precipitate.

The content of the stannous ion in the acidic solution is preferably from 3 to 8% by weight, more preferably 4% by weight. If it is less than 3% by weight, the correcting power of the correction fluid would be insufficient. However, if it is more than 8% by weight, formation of the hydrophilic and water-insoluble chelate would be too much and the corrected part would cause lacking of water. As a result, the aqueous film over the part would be discontinuous and the part would possibly become sensitive to ink.

Such stannous ion is preferably supplied to the aqueous acidic solution in the form of stannous chloride. This is because the compound stannous chloride may be free in the aqueous solution to release hydrochloric acid thereby to lower the pH value of the solution. Additionally, the thus released hydrochloric acid may easily be removed from the solution by drying and therefore the post-treatment is easy. As a matter of course, the stannous ion may also be supplied in any other form of a salt with an organic acid radical such as acetic acid radical or propionic acid radical or an inorganic acid radical.

The pH value of the aqueous solution containing the stannous chelate compound as dissolved therein may be determined in accordance with the ligand of the chelate compound.

As means of elevating the pH value of the aqueous solution containing the stannous chelate compound as dissolved therein, (1) the aqueous solution is neutralized with a base or (2) were the acid radical in the aqueous solution is volatile (for example, it is hydrochloric acid radical, acetic acid radical, propionic acid radical or the like), the aqueous solution is dried (for example, by leaving it as it is in the ambient atmosphere for a while or by applying a room temperature air or a hot air thereto) so as to remove the acid radical from the solution.

The method of preparing the water-soluble stannous chelate compound for use in the present invention is not specifically defined. For instance, a water-insoluble chelate compound is first prepared, this is suspended in water and an acid may be added thereto to convert it into a water-soluble compound. Alternatively, the aqueous solution may be made acidic from the first to directly prepare a water-soluble chelate compound.

It is preferred to incorporate a proper amount of a polar solvent such as alcohols to the aqueous solution containing the stannous chelate compound as dissolved therein, for the purpose of inhibiting hydrolysis of the stannous ion and of elevating the adhesiveness of the solution to the surface of zinc oxide. By addition of a polar solvent to the solution, the anchor effect of the solution is elevated.

Additionally, it is also preferred to incorporate a proper amount of a dicarboxylic acid, such as malonic acid, adipic acid, succinic acid, gluconic acid, p-toluolsulfonic acid or the like, to the solution, for the purpose of smoothly effecting the complexing reaction or chelating reaction with ferrocyan or phytic acid.

As explained in the above, the stannous chelate compound of an acidic phosphate ester of an aliphatic alcohol of the present invention is soluble in an aqueous acidic solution and, after the pH value of the compound-containing aqueous solution has been elevated, the compound gives a precipitate in the solution. Since the thus formed precipitate is hydrophilic, it formed an aqueous film when treated with a wetting water and the film is to repel ink.

Accordingly, the chelate compound of the invention may be coated on the part to be corrected of an electrostatic master paper plate in the form as dissolved in an aqueous acidic solution and the pH value of the chelate compound-containing aqueus acidic solution as applied to the part to be corrected of the electrostatic master paper plate is elevated, whereby the solution forms a hydrophilic and water-insoluble layer to properly coat the part to be corrected of the electrostatic master paper plate. That is to say, the part to be corrected of the electrostatic master paper plate is lipophobicated by the layer coated thereover.

Such treatment may be effected at any stage before or after the lipophobication of the electrostatic master paper plate to be treated. The precipitate layer derived form the chelate compound hardly peels off from the electrostatic master paper plate and hardly breaks down therefrom, during the course while the master paper plate is used for offset printing.

Therefore, the chelate compound-containing correction fluid of the invention may be applied not only to conventional electrostatic master paper plates but also to lipophobicated electrostatic master paper plates as processed by a platemaker combined with a lipophobicating device, with ease and without necessity of re-lipophobication treatment of the plates, whereby the unnecessary line image parts may be removed from the thus treated plates.

EXAMPLES

Next, the examples of the present invention will be explained hereunder.

In the examples, the "stannous chelate compound having an acidic phosphate ester of an aliphatic alcohol as the ligand" was prepared in the form as dissolved in an aqueous acidic solution. That is, the compound-containing solution is the correction fluid of the invention. The proportion of the respective components in the aqueous solution is shown in Table 1 below. In the proportion, where the amount of the hydrochloric acid is lower than that indicated in Table 1, the chelate compound is to precipitate out. Needless to say, the amount of the hydrochloric acid may be increased.

On the other hand, the composition of Comparative Example 1 is same as the basic composition of the correction fluid which is most popularly sold in the commercial market at the present, and the commercial correction fluid is used prior to lipophobication.

Comparative Examples 2 and 3 are to examine the content of the stannous ion to be incorporated into the correction fluid. Comparative Examples 4 and 5 are to examine the proportion of the stannous ion to the ligand.

The correction fluids as indicated in Table 1 were used as mentioned below.

First, an electrostatic master paper plate was processed by an orinary electrophotomechanical process to prepare a processed plate.

The processed plate was introduced into an etching processer, using a commercial ferrocyan or phytic acid-containing lipophobicating solution, whereby the plate was lipophobicated.

Each of the correction fluids of Examples 1 to 9 was coated on the line image part of the thus lipophobicated processed plate and dried thereon by allowing it to stand as it was for several minutes. Afterwards, the processed plate was set in a printing machine and printing was started immediately, whereupon the printing ink first adhered to the complete surface of the processed plate as the plate was in a dry state, but after water was applied thereto, the surface of the plate gradually became clear to give normal prints. In the procedure, the printing ink did not adhere to the part as coated with the dry layer of the correction fluid. Even after 3000 copies were printed, no copies were stained. Accordingly, the ink-repellent nature of the part as coated with the dry layer of the correction fluid of each Example was well maintained during the printing procedure.

On the other hand, where the correction fluid of Comparative Example 1 was used, the printing ink could not be removed from the surface as coated with the correction fluid even after water was applied thereto during running of the printing machine and, as a result, the complete surface of the plate as coated with the correction fluid was stained with the printing ink. After continuous printing with the plate, the ink could not still be removed from the coated surface.

Next, after the correction fluid of each Example was coated and dried on the processed plate, (2) the plate was previously wetted with a wetting water prior to initiation of printing, whereby normal prints were obtained immediately after the initiation of printing. Precisely, since no ink adhered to the correction fluid-coated part, there was no trouble even after the printing of 3000 copies.

On the other hand, however, where the correction fluid of Comparative Example 1 was used in the same procedure, a noticeable amount of the printing ink still remained on the correction fluid-coated surface, although the degree of the stains to be caused by the remaining ink was not so much as the above-mentioned case (1). Therefore, the correction fluid was not practically usable. Additionally, after 100 copies were printed, the correction fluid of Comparative Example 1 as coated on the printing plate was lost, and the unnecessary line images appeared on the printing copies.

Where the correction fluids of Comparative Examples 2 to 5 were tested in the same manner as above, a noticeable amount of the printing ink also remained on the corrected part and the printed copies were thereby stained.

Where the correction fluid of each Example was coated and dried on the line image part of the processed plate prior to the lipophobication treatment of the plate and thereafter the thus coated plate was lipophobicated, no stain occurred in the corrected parts of the printed copies. This was same even after 3000 copies were printed. The property of the correction fluid of each Example is comparable to that of the correction fluid of Comapative Example 1 in this respect.

Table 2 below shows correction fluids of Examples 10, 11 and 12, which were prepared by adding an adhesion accelerator and/or a complexing reaction accelerator to the correction fluid of Example 2.

Where the correction fluid of each of these Examples was partly coated and dried on an electrostatic master paper plate, no ink adhered to the coated part. The thus coated plate was used in printing, and normal 3000 copies were obtained from the initial stage of the printing procedure.

In the above-mentioned printing operation, the number of the copies to be printed with the processed plate was limited to 3000 copies in view of the life of the electrostatic master paper plate used. However, it may be expected that the alcohol-containing correction fluids of Examples 10 and 12 would have a higher durability than the correction fluid of Example 2 bacause of the hydrolysis-inhibiting effect and the anchor effect of the alcohol. Additionally, it may also be expected that the dicarboxylic acid-containing correction fluids of Examples 11 and 12 would have a higher durability than the correction fluid of Example 2 when they are used prior to the lipophobication treatment of the electrostatic master paper plate, since the complexing reaction with the ferrocyan or phytic acid is accelerated.

6. A correction fluid for correcting an unwanted line image part of an electrostatic master paper plate, comprising:
(a) an aqueous acidic solution, and
(b) a hydrophilic stannous chelate compound consist-

TABLE 1

|  | Examples | | | Comparative Examples | | Example | Comparative Examples | | Examples | | | | | Comparative Example |
|---|---|---|---|---|---|---|---|---|---|---|---|---|---|---|
|  | 1 | 2 | 3 | 2 | 3 | 4 | 4 | 5 | 5 | 6 | 7 | 8 | 9 | 1 |
| Stannous Chloride | 8.0 | 6.0 | 15.0 | 5.0 | 17.0 | 8.0 | 8.0 | 8.0 | 8.0 | 8.0 | 8.0 | 8.0 | 8.0 | 8.0 |
| (stannous ion) | (4.2) | (3.2) | (7.9) | (2.6) | (9.0) | (4.2) | (4.2) | (4.2) | (4.2) | (4.2) | (4.2) | (4.2) | (4.2) | (4.2) |
| Hydrochloric Acid | 18.0 | 18.0 | 18.0 | 18.0 | 18.0 | 18.0 | 18.0 | 18.0 | 7.5 | 6.0 | 4.0 | 5.5 | 18.0 | 6.0 |
| Water | 56.0 | 56.0 | 56.0 | 56.0 | 56.0 | 56.0 | 56.0 | 56.0 | 78.5 | 77.0 | 76.0 | 74.5 | 64.0 | 86.0 |
| Phytic Acid | 18.0 | 13.5 | 33.8 | 11.3 | 38.3 | 10.8 | 7.2 | 21.6 |  |  |  |  | 6.0 |  |
| (chelate equivalency) | [1] | [1] | [1] | [1] | [1] | [0.6] | [0.4] | [1.2] |  |  |  |  | [1/3] |  |
| Acidic Methyl Phosphate |  |  |  |  |  |  |  |  | 6.0 |  |  |  | 4.0 |  |
| (chelate equivalency) |  |  |  |  |  |  |  |  | [1] |  |  |  | [2/3] |  |
| Acidic Ethyl Phosphate |  |  |  |  |  |  |  |  |  | 9.0 |  |  |  |  |
| (chelate equivalency) |  |  |  |  |  |  |  |  |  | [1] |  |  |  |  |
| Acidic n-propyl Phosphate |  |  |  |  |  |  |  |  |  |  | 12.0 |  |  |  |
| (chelate equivalency) |  |  |  |  |  |  |  |  |  |  | [1] |  |  |  |
| Acidic isopropyl Phosphate |  |  |  |  |  |  |  |  |  |  |  | 12.0 |  |  |
| (chelate equivalency) |  |  |  |  |  |  |  |  |  |  |  | [1] |  |  |
| Results | ○ | ○ | ○ | X | X | ○ | X | X | ○ | ○ | ○ | ○ | ○ | X |

Notes:
(1) All numerical values in Table 1 are parts by weight. The values as parenthesized indicate the chelate equivalency to the stannous ion.
(2) For the results, the mark "○" indicates that the printed copies had no stain in the corrected part, where the correction liquid having the ingredients shown in Table 1 was coated on the image part of the lipophobicated electrostatic master paper plate and dried thereon; while the mark "X" indicates that the printed copies has stains.
(3) the phytic acid used is a commercial product manufactured by Mitsui Toatsu Chemical Co.; and the other esters were prepared by the inventor himself.

TABLE 2

|  | Example 10 | Example 11 | Example 12 |
|---|---|---|---|
| Stannous Chloride | 6.0 | 6.0 | 6.0 |
| (stannous ion) | (3.2) | (3.2) | (3.2) |
| Hydrochloric Acid | 18.0 | 18.0 | 18.0 |
| Water | 22.0 | 22.0 | 22.0 |
| Phytic Acid | 13.5 | 13.5 | 13.5 |
| (Chelate equivalency) | [1] | [1] | [1] |
| Ethanol | 34.0 | — | 34.0 |
| Malonic Acid | — | 1.0 | 1.0 |
| Results | ○ | ○ | ○ |

What is claimed is:

1. A hydrophilic stannous chelate compound consisting of stannous ion and an acidic phosphate ester of an aliphatic alcohol as a ligand, wherein the proportion of the salt acidic phosphate ester of an aliphatic alcohol to the said stannous ion is from 0.5/1.0 to 1.0/1.0.

2. The stannous chelate compound as defined in claim 1, wherein the proportion of the said acidic phosphate ester of an aliphatic alcohol to the said stannous ion is 1.0/1.0 in view of the chelating equivalency therebetween.

3. The stannous chelate compound as defined in claim 1, wherein the said ligand is one or more selected from acidic phosphate esters of aliphatic lower alcohols and acidic phosphate esters of alicyclic alcohols.

4. The stannous chelate compound as defined in claim 3, wherein the said acidic phosphate ester of an aliphatic lower alcohol is at least one member selected from the group consisting of acidic methyl phosphate, acidic ethyl phosphate, acidic propyl phosphate and acidic isopropyl phosphate.

5. The stannous chelate compound as defined in claim 3, wherein the said acidic phosphate ester of an alicyclic alcohol is phytic acid.

6. A correction fluid for correcting an unwanted line image part of an electrostatic master paper plate, comprising:
(a) an aqueous acidic solution, and
(b) a hydrophilic stannous chelate compound consisting of stannous ion and an acidic phosphate ester of an aliphatic alcohol as the ligand, wherein the proportion of the said acidic phosphate ester of an aliphatic alcohol to the said stannous ion is from 0.5/1.0 to 1.0/1.0;
wherein (c) the content of the stannous ion to be contained in the said stannous chelate compound is from 3 to 8% by weight to the complete aqueous solution.

7. The correction fluid as defined in claim 6, wherein the content of the stannous ion to be contained in the said stannous chelate compound is 4% by weight to the complete aqueous solution.

8. The correction fluid as defined in claim 6, wherein the proportion of the said acidic phosphate ester of an aliphatic alcohol to the said stannous ion is 1.0/1.0 in view of the chelating equivalency therebetween.

9. The correction fluid as defined in claim 6, wherein the said ligand is one or more selected from acidic phosphate esters of aliphatic lower alcohols and acidic phosphate esters of alicyclic alcohols.

10. The correction fluid as defined in claim 9, wherein the said acidic phosphate ester of an aliphatic lower alcohol is at least one member selected from the group consisting of acidic methyl phosphate, acidic ethyl phosphate, acidic n-propyl phosphate and acidic isopropyl phosphate.

11. The correction fluid as defined in claim 9, wherein the said acidic phosphate ester of an alicyclic alcohol is phytic acid.

12. The correction fluid as defined in claim 6, wherein the acid radical of the said aqueous acidic solution is volatile.

13. The correction fluid as defined in claim 12, wherein the said volatile acid radical is one member selected from the group consisting of hydrochloric acid, acetic acid and propionic acid.

14. The correction fluid as defined in claim 6, which further comprises at least one adhesion accelerator or at least one complexing reaction accelerator.

15. The correction fluid as defined in claim 14, wherein the said adhesion accelerator is a polar solvent.

16. The correction fluid as defined in claim 15, wherein the said polar solvent is an alcohol.

17. The correction fluid as defined in claim 14, wherein the complexation accelerator is a dicarboxylic acid selected from the group consisting of malonic acid, adipic acid, succinic acid, gluconic acid and p-toluolsulfonic acid.

18. A correction fluid for correcting an unwanted line image part of an electrostatic master plate, essentially consisting of:
  (a) an aqueous acidic solution, and
  (b) a hydropholic stannous chelate compound consisting of stannous ion and an acidic phosphate ester of an aliphatic alcohol as a ligand, wherein the proportion of the said acidic phosphate ester of an aliphatic alcohol to the said stannous ion is from 0.5/1.0 to 1.0/1.0;
wherein (c) the content of the stannous ion to be contained in the said stannous chelate compound is from 3 to 8% by weight to the complete aqueous solution.

19. A method of erasing an unwanted line image part of an electrophoto plate for offset printing, comprising:

(a) a correction fluid-preparing step, where a stannous chelate compound having an acidic phosphate ester of an aliphatic alcohol as the ligand is dissolved in an aqueous acidic solution to prepare the correction fluid;
  (b) a coating step, where the correction fluid is coated on an unwanted line image part of an electrophoto plate for offset printing; and
  (c) a precipitation step, where the pH value of the said correction fluid is elevated to precipitate said stannous chelate compound on the said unwanted line image part, said precipitated stannous chelate compound being hydrophilic and attracting an aqueous film to repel printing ink, thereby erasing said unwanted line image part.

20. The method of erasing the unnecessary line image part of an electrophoto plate for offset printing as defined in claim 19, wherein an alkali is added to the said correction fluid so as to elevate the pH value of the fluid in the said precipitation step.

21. The method of erasing the unnecessary line image part of an electrophoto plate for offset printing as defined in claim 19, wherein the said stannous chelate compound is dissolved in an aqueous acidic solution containing a volatile acid radical in the said correction fluid-preparing step, and the said volatile acid radical is evaporated out from the correction fluid so as to elevate the pH value of the fluid in the said precipitation step.

* * * * *